United States Patent

Matsuno et al.

[11] Patent Number: 5,342,394
[45] Date of Patent: Aug. 30, 1994

[54] APPARATUS FOR BLOCKING A VEIN BRANCH AND METHOD OF BLOCKING A VEIN BRANCH

[75] Inventors: Kiyotaka Matsuno; Masahiro Kawashima; Akio Nakada, all of Tokyo, Japan

[73] Assignee: Olympus Optical Co., Ltd., Tokyo, Japan

[21] Appl. No.: 979,439

[22] Filed: Nov. 20, 1992

Related U.S. Application Data

[63] Continuation of Ser. No. 644,110, Jan. 18, 1991, abandoned.

[30] Foreign Application Priority Data

| | | | |
|---|---|---|---|
| May 16, 1990 | [JP] | Japan | 2-50302[U] |
| Aug. 6, 1990 | [JP] | Japan | 2-207816 |
| Oct. 25, 1990 | [JP] | Japan | 2-287858 |

[51] Int. Cl.⁵ .................. A61B 17/08; A61D 1/00
[52] U.S. Cl. ................... 606/213; 604/15; 604/22; 604/60; 604/165; 604/166; 604/167; 606/159
[58] Field of Search ............ 604/14–16, 604/22, 59, 60, 93, 96, 103, 158, 160, 164–166, 170, 171, 264, 280–282, 285, 286; 606/108, 167, 159, 170, 191, 190, 195, 198, 213, 215; 128/655, 656, 658, 772, 831, 843

[56] References Cited

U.S. PATENT DOCUMENTS

| | | | |
|---|---|---|---|
| 3,719,737 | 3/1973 | Vaillancourt et al. | 604/281 |
| 3,805,767 | 4/1974 | Erb . | |
| 3,867,945 | 2/1975 | Long | 606/108 |
| 4,299,226 | 11/1981 | Banka | 128/657 |
| 4,512,345 | 4/1985 | Green . | |
| 4,512,765 | 4/1985 | Muto | 604/281 |
| 4,586,923 | 5/1986 | Gould et al. | 128/657 |
| 4,744,364 | 5/1988 | Kensey | 606/213 |
| 4,801,297 | 1/1989 | Mueller | 604/280 |
| 4,898,577 | 2/1990 | Badger et al. | 604/282 |
| 4,994,069 | 2/1991 | Ritchart et al. | 604/104 |

FOREIGN PATENT DOCUMENTS

| | | |
|---|---|---|
| 0105669 | 4/1984 | European Pat. Off. . |
| 59-82854 | 5/1984 | Japan . |
| 63-38505 | 3/1988 | Japan . |
| 64-2639 | 1/1989 | Japan . |

*Primary Examiner*—Rosenbaum, C. Fred
*Assistant Examiner*—Ronald Stright, Jr.
*Attorney, Agent, or Firm*—Frishauf, Holtz, Goodman & Woodward

[57] ABSTRACT

An apparatus for blocking a vein branch is provided with an outer tube having a tubular passage opened at its distal and proximal ends and a bent distal end portion, an inner tube slidably inserted in the outer tube so as to be projected and retracted from the opening formed in the distal end portion of the outer tube and having a storing portion filled with a vein-branch blocking member, and a push-out member for pushing out the blocking member in the vein branch.

17 Claims, 5 Drawing Sheets

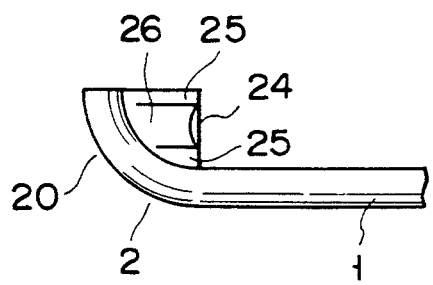
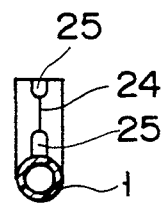
F I G. 6     F I G. 7
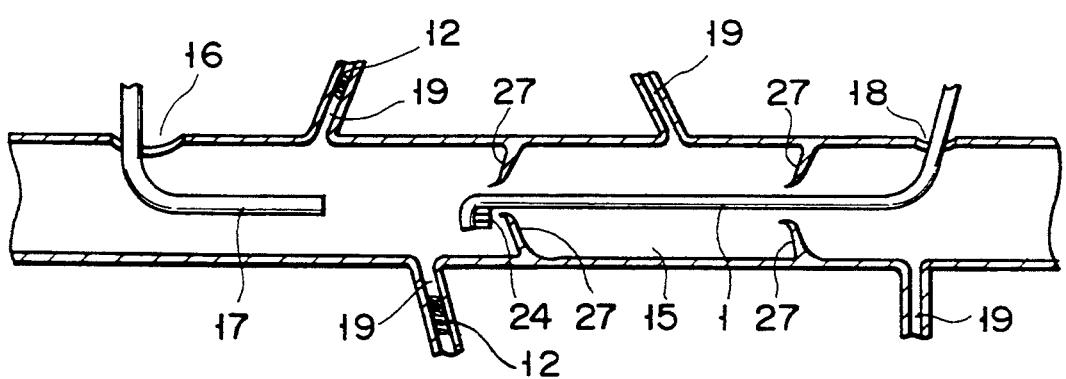
F I G. 8

5,342,394

APPARATUS FOR BLOCKING A VEIN BRANCH AND METHOD OF BLOCKING A VEIN BRANCH

This application is a continuation of application Ser. No. 07/644,110, filed Jan. 18, 1991, now abandoned.

BACKGROUND OF THE INVENTION

1. Field of the Invention

This invention relates to an apparatus for and a method of blocking a vein branch.

2. Description of the Related Art

Recently, a surgical operation has been performed for bypassing, by means of a saphena, a blocked artery which causes stasis of blood stream due to thrombus or atheroma in a leg. Since a part of a vein is used as a part of a damaged artery in this surgical operation, it is necessary to cut the venous valve of the vein. In doing so, openings are formed at the upstream and downstream portions of the vein to be cut, and the vein is clamped at the vicinity of those openings to be blocked. Thereafter, a cutting apparatus is inserted from the upstream opening in the vein so as to be placed at its required position and then pulled to cut the vein. As a vein has a lot of vein branches, it is necessary to block them at the vicinity of the vein by means of a blocking apparatus.

Japanese Laid-open Patent Application No. 64-2639 discloses a clipping apparatus, as an example of a vein-branch blocking apparatus, for blocking a vein branch externally by surgically cutting a living body in order to prevent blood from flowing in the vein branch. With this clipping apparatus, a scissor-like clip is pushed out from the vein by means of a push-out member so that the vessel is flattened to be blocked. Alternatively, the vessel is blocked by a thread or the like.

In the conventional surgical operation for bypassing a membrum inferius as described above, the related portion is cut along the vein portion used as a bypass of an damaged artery and then the vein branches are externally blocked by clips, threads or the like. This method is encountered with the problem that the surgically operated patient must stay in a hospital for a long time until he or she is cured from disease because the related portion is cut by a long length along the vein portion to be used for bypassing the artery.

The conventional surgical operation method is also met by a problem that it is difficult to cut the required portion accurately because it needs the step for checking the positions of the vein branches by the use of a vein cutting apparatus disposed in the vein portion. In addition, this method requires a long time.

SUMMARY OF THE INVENTION

The object of this invention is to provide an apparatus for blocking a vein branch which ensures the accurate blocking of a vein branch in a short time by minimizing the surgically cut length of a vein.

This object is attained by an apparatus for blocking a vein branch comprising a tubular passage opening at its distal end and proximal end, an outer tube having a bent front end, an inner tube inserted slidably into the outer tube so as to be projected and retracted from the opening of the distal end of the outer tube, the inner tube having a storing portion for filling a blocking member for blocking a vein branch and means for pushing out the blocking member into the vein branch.

The blocking of the vein branch carried out in the interior of the vein reduces the length of the living body to be cut and allows surgical operation to be simplified and the patient to be cured in a shorter time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 6 is a lateral side view of the distal end portion of the fourth embodiment of an apparatus for blocking a vein branch;

FIG. 7 is a rear view of the distal portion of FIG. 6;

FIG. 8 is a schematic view illustrating the usage of the apparatus of the fourth embodiment;

DETAILED DESCRIPTION OF THE PREFERRED EMBODIMENTS

This invention will be explained in detail by way of preferred embodiments with reference to the accompanying drawings.

Figure 1:
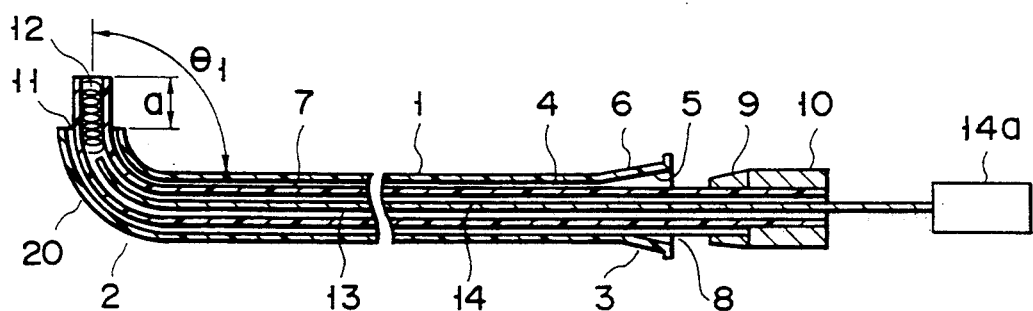
FIG. 1 is a longitudinal cross-sectional view of the first embodiment of an apparatus for blocking a vein branch.

FIG. 1 shows an apparatus for blocking a vein branch of the first embodiment. The apparatus includes an outer tube 1 which has an distal end 2, a proximal end 3 and a tubular passage 4 opened at both ends 2 and 3. The forward end of the outer tube 1 is bent at an angle $\theta_1$ ranging from 60° to 120° with respect to main portion of the outer tube 1, and the proximal end portion 3 is provide with a mount 6 having an inner tapered face 5.

An inner tube 7 made of a flexible material is inserted in the tubular passage 4 from the opening 8 at the proximal end of outer tube 1. To the proximal end of the inner tube 7 is fixed a grip 10 having an outer tapered portion 9 which can be inserted in the inner tapered portion 5 of the mount 6 and fixed thereto. The length of the projection a of the inner tube 7 from the opening 11 at the distal end of the outer tube 1 is adjusted to substantially 10 to 30 mm.

Figure 2:
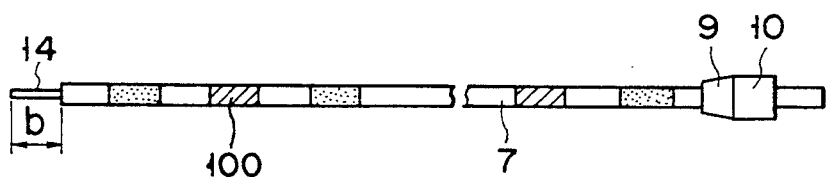
FIG. 2 is a lateral side view of the inner tube of the apparatus of the first embodiment.

As shown in FIG. 2, markings 100 are formed on the outer periphery of the distal end portion and the proximal end portion of the inner tube 7 at equal intervals so that the inserted length and the projecting length of the inner tube 7 can be observed externally. The inner tube 7 has a tubular passage 13 which is filled with a blocking member 12 in its distal end portion and allows a push-out member 14 consisting of a flexible bar-like member to be reciprocatingly inserted thereinto from its distal end.

The push-out member 14 is provided on its proximal end with an operation portion 14a. The blocking member 14 filled in the distal end portion of the inner tube 7 can be pushed out forwardly by projecting the push-out member 14 from the distal end of the inner tube 7. The maximum projected length b of the push-out member 14 from the inner tube 7 is limited to substantially 15 mm or less. The blocking member 12 pushed out from the distal end of the inner tube 7 assumes a coil form and has attached to each coil element many hairs which are rounded after the coil elements are pushed out from the inner tube 7 so that the hairs easily stop blood flow in a vein branch.

The operation of the first embodiment of the apparatus for blocking a vein branch according to the first embodiment of this invention will now be explained.

Figure 3:
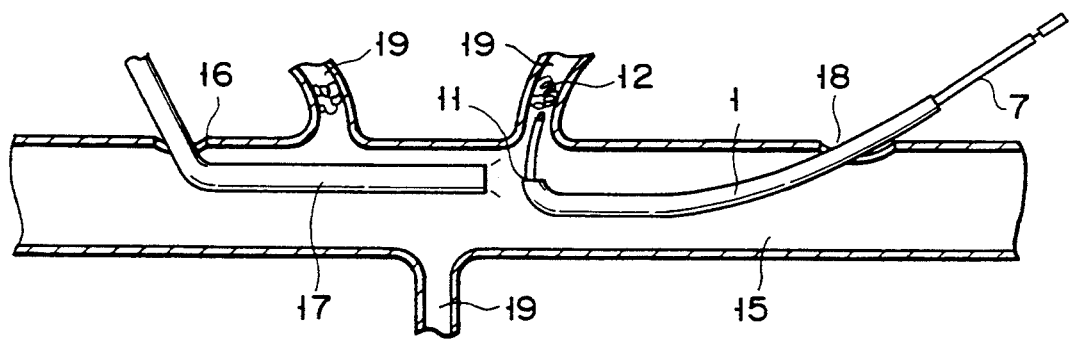
FIG. 3 is a schematic view illustrating the usage of the apparatus of the first embodiment.

As shown in FIG. 3, openings 16 and 18 are formed in the two required portions of a vein 15 to be used. A fiberscope or a blood-vessel scope 17 is inserted in the vein 15 from one of the openings 16 and the apparatus for blocking a vein branch is inserted in the vein 15 from the other opening 18. Then, a vein branch 19 is blocked by observing the vein branch 19 and the distal end portion of the outer tube 1.

The outer tube 1 is inserted in the vein 15 from the opening 18 until the opening 11 at the distal end of the outer tube 1 is placed at the position facing the branched portion of the vein branch 19 to be blocked. Then, by observing the markings formed on the distal end portion of the inner tube 7, the inner tube 7 filled with the blocking member 12 is inserted into the tubular passage 4 of the outer tube 1 from the opening 8 at its proximal end portion, until the distal end portion of the inner tube 7 is correctly disposed in the vein branch 19. Thereafter, the inner tube 7 is fixed to the outer tube 1 by mating the tapered portion 9 of the grip 10 with the tapered portion 5 of the outer tube 1. Finally, by holding the outer tube 1, the blocking member 12 is pushed out from the inner tube 7 into the vein branch 19 and then retained there so as to block the vein branch 19.

Since the vein branch 19 is blocked by the blocking member 12 supplied by the outer tube 1 disposed in the vein 15, the cut-out length of the living body is shortened, enabling the surgical operation to be simplified. The patient is cured from disease very fast, shortening his or her stay in the hospital.

The bending of the distal portion of the outer tube 1 at an angle between 60° and 120° allows the inner tube 7 to be easily inserted in the vein branch 19 branched from the lateral wall of the vein 15. Because it is confirmed by the markings formed on the distal end portion of the inner tube 7 how many centimeters the distal end portions of the inner tube 7 is inserted in the vein branch 19, the blocking of the vein branch 19 is ensured. The use of the markings on the proximal end portion of the inner tube 7 permit the projected length of the distal end portion of the inner tube 7 to be confirmed at the side of the operator, preventing the inner tube 7 from being projected excessively into the vein branch 19 due to carelessness, thereby hindering the inner wall of the vein branch 19 from being damaged. The blocking of the vein branch 19 is performed under the observation by means of a fiberscope. This ensures safe blocking of the vein branch 19.

Figure 4:
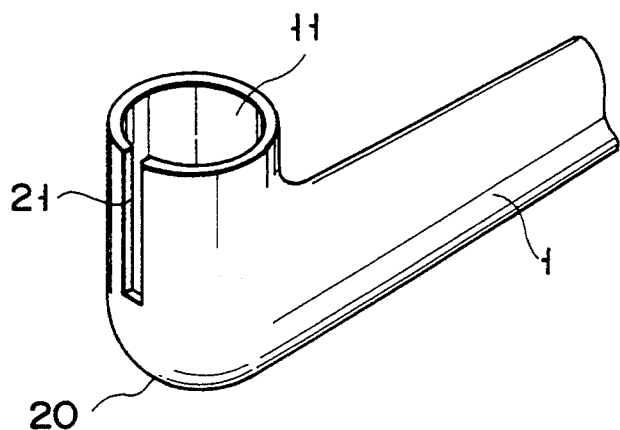
FIG. 4 is a perspective view of the distal portion of the outer tube of the second embodiment of an apparatus for blocking a vein branch.

FIG. 4 illustrates the second embodiment of this invention in which the structure of the apparatus for blocking a vein branch is the same as that of the first embodiment, excepting that the bent distal end portion 20 of an outer tube 1 is made of a transparent material such as transparent resin.

With this apparatus according to the second embodiment, the projecting amount of an inner tube 7 can be known by observing the markings formed on the distal end portion of the inner tube 7 through the transparent bent distal end portion of the outer tube 1, even if the opening 11 at the distal end of the outer tube 1 is disposed so close to the vein branch 19 that the projecting amount of the inner tube 7 in the vein branch 19 cannot be observed by means of the fiberscope 17.

As shown in FIG. 4, a slit 21 may be formed at the distal portion of the bent distal end portion 20 so that the markings on the distal end portion of the inner tube 7 can directly been observed therethrough.

Figure 5:
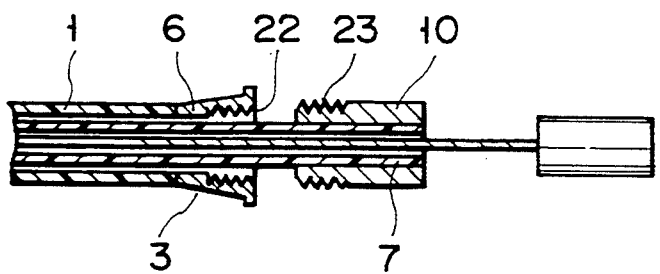
FIG. 5 is a longitudinal cross-sectional view of the proximal end portion of the third embodiment of an apparatus for blocking a vein branch.

In FIG. 5 is shown the third embodiment of this invention, in which a female thread 22 is formed in the inner wall of the mount 6 of an outer tube 1 and a male thread 23 is formed in the outer wall of the distal end portion of the grip 10 of an inner tube 7 so as to engage the female thread 22. The other structure of the third embodiment is the same as that of the first embodiment.

When the male thread 23 is screwed into the female thread 22 by adjusting the degree of engagement between the outer tube 1 and the inner tube 7, the inner tube 7 is fixed to the outer tube 1 at its arbitrary position. In other words, by adjusting the projecting length of the inner tube 7 from the outer tube 1, the blocking member 12 is positioned at the suitable position in the vein branch 19.

In FIGS. 6 to 8 is shown the fourth embodiment of this invention in which the inside outer periphery of the bent portion 20 at the distal end portion 2 of the outer tube 1 is provided with a chip 26 which comprises a holding part 25 having a smooth outer surface and a cutting edge 24 formed on a central portion of the holding portion 25. The other structure of the fourth embodiment is the same as that of the first embodiment.

The operation of the apparatus for blocking a vein branch according to the fourth embodiment will now be explained with reference to FIG. 8 which shows how to cut a venous valve 27 by means of the chip 26.

The outer tube 1 is inserted in the vein 15 from the previously formed upstream side opening 18, and the fiberscope 17 is inserted therein from the downstream side opening 16. After then, the inner tube 7 is set at a position in which the chip 26 is disposed at the proper location close to the venous valve 27 and the outer tube 1 is pulled toward its proximal side, thereby easily cutting the venous valve 27 by means of the cutting edge 24 of the chip 26.

The cutting of the venous valve 27 and the blocking of the vein branch 19 can be performed in a serial process. The vein 15 is similarly blocked in the case of the first embodiment.

In the general bypassing operation of a vein, the cutting a vein and the blocking operation of a vein branch or branches are effected in a serial process. Provision of a cutting edge for removing a venous valve on an apparatus for blocking a vein branch makes it unnecessary to carry out interchange between the apparatus for blocking a venous branch and an apparatus for cutting a vein branch when a surgical operation of the vein is performed, thereby simplifying the process of the operation.

Figure 9:
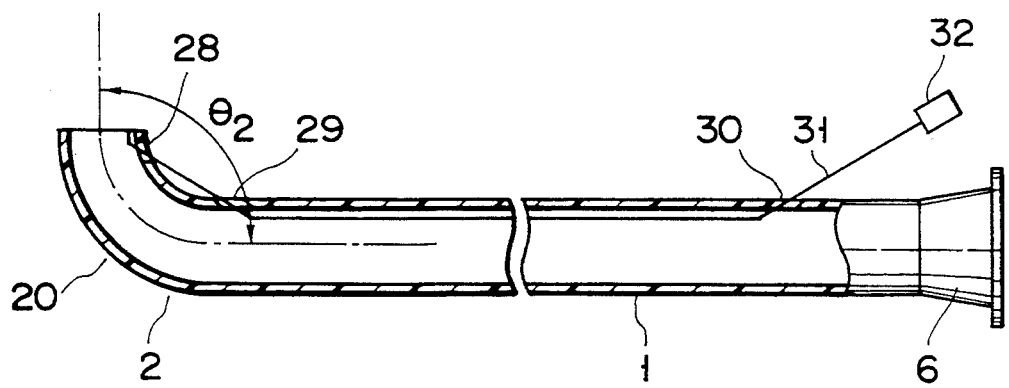
FIG. 9 is a cross-sectional view of the outer tube of the fifth embodiment of an apparatus for blocking a vein branch.

FIG. 9 illustrates the fifth embodiment of this invention.

The whole outer tube 1 is made of a soft, flexible material. A first hole 28 is formed in a portion of the outer tube 1 which is slightly separated from its distal end toward its proximal end, and a second hole 29 is formed in a portion of the outer tube 1 which is slightly departed from the first hole 28 toward the proximal end of the outer tube 1. Further, a third hole 30 is formed in the peripheral wall of the outer tube 1 at the vicinity of a mount 6. The holes 28, 29 and 30 lie at their axes on a plane including the axis of the outer tube 1 and have a wire 31 passing therethrough. The wire 31 is fixed at its proximal end to a grip portion 32. It is extended outside of the outer tube 1 between the holes 28 and 28 and between the hole 30 to the grip portion 32 and it also extends in the portion of the outer tube 1 between the holes 29 and 30. The wire 31 is fixed to those portions of the inner wall of the outer tube 1 which are adjacent to the holes 28 and 29.

when the operator pulls the wire 31 toward the proximal end of the outer tube 1, the distal end of the outer tube 1 is pulled in the same direction to curve the distal end bent portion 20 at a required angle $\theta_2$ by adjusting the pulled amount of the wire 31, facilitating the blocking of a vein branch 19. The other structure and operation of the apparatus of the fifth embodiment are the same as those of the first embodiment.

Figure 10:
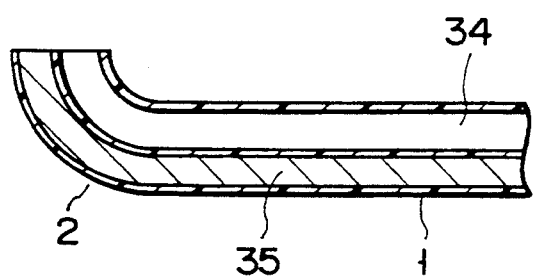
FIG. 10 is a longitudinal cross-sectional view of the outer tube of the sixth embodiment of an apparatus for blocking a vein branch.
Figure 11:
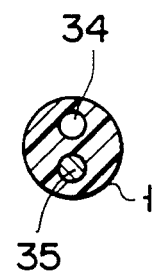
FIG. 11 is a transverse cross-sectional view of the outer tube of the sixth embodiment.

The sixth embodiment of this invention will now be explained with reference to FIGS. 10 and 11, which embodiment has two tubular passages 34. In one of the tubular passages 34 is a wire 35 which is harder than the outer tube 1 is inserted under pressure so that the outer tube 1 is bent laterally in accordance with the curvature of the wire 35.

With the sixth embodiment, therefore, the bending angle of the distal end portion 2 of the outer tube 1 can be easily determined in accordance with the degree of bending of the wire 35 inserted in the outer tube 1. In the other tubular passage 34 is inserted an inner tube 7. The other structure and operation are the same as those of the first embodiment.

Figure 12:
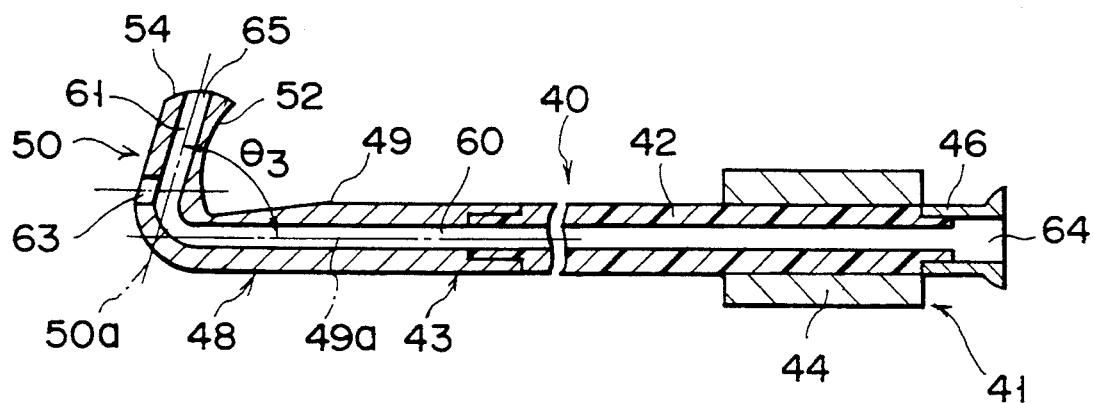
FIG. 12 is a longitudinal cross-sectional view of the seventh embodiment of an apparatus for blocking a vein branch.
Figure 13:
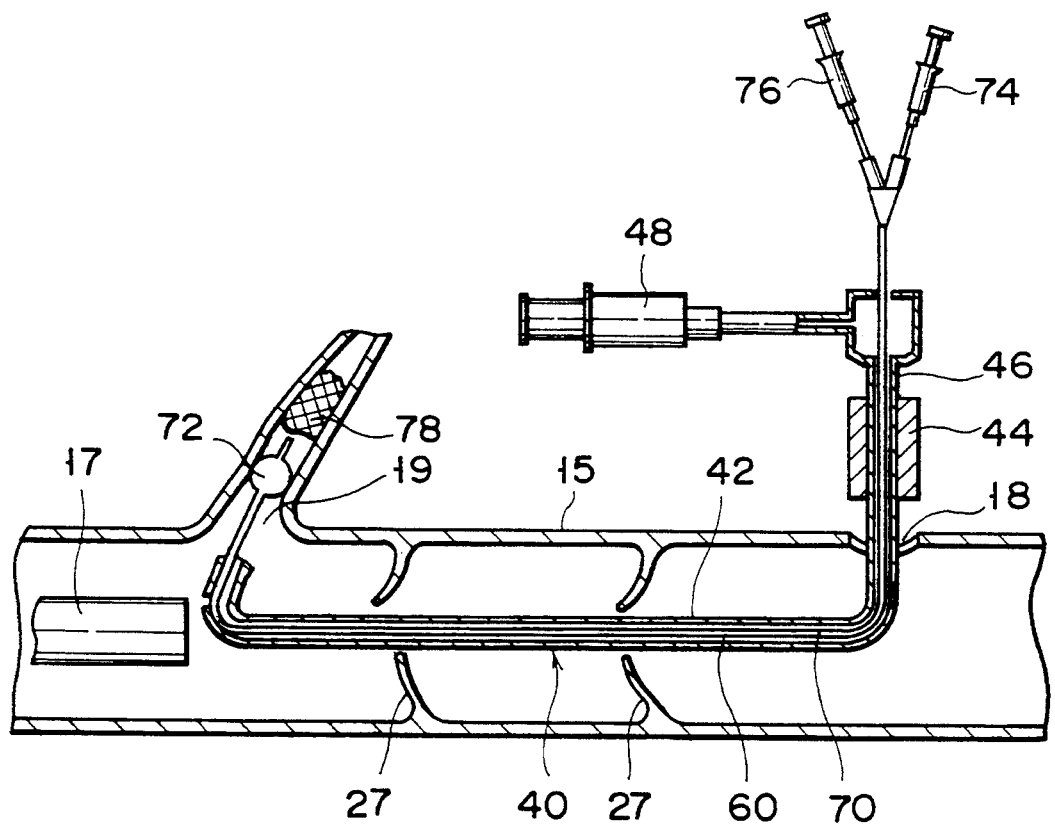
FIG. 13 is a schematic view illustrating the usage of the apparatus of the seventh embodiment.

Referring to FIGS. 12 and 13, the seventh embodiment of this invention will now be described.

As shown in FIG. 12, an apparatus 40 for cutting a vein branch has a flexible sheath 42. To the operating portion 41 provided on the proximal end of the flexible sheath 42 is fixed a grip portion 44 by means of a screw or the like. A mount 46, to which syringes is Joined, is connected to the grip portion 44. A rigid portion 48 is fixed to the distal end 43 of the flexible sheath 42 by means of screw means or the like.

As shown in FIG. 12, the rigid portion 48 comprises a main body section 49 and a bent section 50 curved at the distal end of the main body section 49. The bent section 50 comprises a blade 52 having a cutting edge at its proximal end and a hemispherical head 54. The bent section 50 is curved so that the axis 50a of the bent section 50 is inclined at an angle $\theta_3$ less than 90°.

With the apparatus 40 for blocking a vein branch of the seventh embodiment, the flexible sheath 42, the mount 46 and the body section 49 of the rigid portion 48 are all hollow and the whole length of the hollow portions of them forms a tubular passage 60, when they are connected to one after another so that the passage 60 opens at an opening 65 formed on the distal end of the main body section 49 of the rigid portion 48 and at an opening 64 formed on the proximal end of the mount 46 as shown in FIG. 12.

A syringe 148 (see FIG. 13) is connected to mount 64 to supply water into the flexible sheath 42. The tubular passage 60 communicates with an opening 63 formed in the front portion of the bent section 50 of the rigid portion 48, the opening 63 having an axis in parallel with the axis 49a of the main body section 49 and used as a fluid injecting outlet which injects fluid such as water forwardly.

The operation of the apparatus for blocking a vein branch according to the seventh embodiment will now be explained with reference to FIG. 13.

First, the flow of blood in the vein 15 to be blocked is stopped by blocking the required upstream and downstream portions of the vein 15, and then these portions are cut to form the openings 16 and 18 having a required size. The apparatus 40 for blocking a vein branch is inserted into the vein 15 from the upstream opening 18, and the fiberscope 17 is likewise inserted in the vein 19 from the downstream opening 16.

Next, a balloon catheter 70 is inserted in the tubular passage 60 of the apparatus 40 for blocking a vein branch so that the balloon 72 of the balloon catheter 70 is disposed in the vein branch 19 in a shrunk state. Then, compressed air is supplied to the balloon 72 from the air-supplying syringe 74 connected to the proximal end of the catheter 70 and inflates the balloon 72 so as to cause the balloon 72 to block the vein branch 19. Further, a coagulant 78 is injected from another syringe 76 connected to the proximal end of the catheter 70 (FIG. 13) into the vein branch 19 to close it.

with the apparatus 40 for blocking a vein branch according to the seventh embodiment, therefore, the vein branch 19 can be observed in a wide visual field of the fiberscope 17 by directly supplying a physiological saline solution to the objective of the fiberscope 17 and the vicinity thereof, thereby reducing the processes for the surgical operation since it is unnecessary to use a conventional catheter with water-supplying means. Since the balloon catheter 70 can be inserted in the vein branch 19 through the tubular passage 60 of the apparatus 40 for blocking a vein branch, it is unnecessary to interchange the treating instruments as is made in the conventional vein-branch blocking apparatus, thereby shortening and simplifying the surgical operation of a vein.

Further, with the apparatus 40 of the seventh embodiment, the bent section 50 of the rigid portion 48 can be disposed close to the required vein branch 19 and the balloon catheter 70 can be inserted in the vein branch 19 from the distal end opening 65 of the bent section 50. This arrangement allows the vein branch 19 to be easily blocked in a short time.

This invention is not limited to the above-mentioned embodiments but various modifications are available within the scope of this invention.

What is claimed is:

1. An apparatus for blocking a vessel branch, comprising:
    an outer tube having a tubular passage therethrough, said tubular passage having an opening at a distal end of said outer tube and an opening at a proximal end of said outer tube, and said outer tube having a bent distal end portion which is bent at an angle of from 60° to 120°;
    an inner tube slidably inserted in the tubular passage of said outer tube so as to have a portion which is projected from and retracted from the opening at the distal end of said tubular passage, said inner tube being made of a flexible material, and said inner tube having a storing portion at a distal end thereof;
    a blocking member contained in said storing portion of said inner tube;
    means for pushing out said blocking member from said storing portion into a vessel branch; and
    cutting means provided on a rear side of said bent distal end portion of said outer tube, for cutting a venous valve of a vein.

2. An apparatus according to claim 1, further comprising means for measuring a length of the portion of said inner tube which is projected from said opening at the distal end of said outer tube, said measuring means being formed on or as part of said outer tube or said inner tube.

3. The apparatus according to claim 2, wherein said measuring means comprises markers formed on an outer periphery of said inner tube.

4. The apparatus according to claim 2, wherein a portion of said outer tube is made of transparent material such that said inner tube can be observed therethrough.

5. The apparatus according to claim 1, further comprising angle adjusting means for adjusting said bent angle of the bent distal end portion of said outer tube, said angle adjusting means including a member having a wire shape, one end of said wire shaped member being connected to the distal end portion of said outer tube, said wire shaped member extending through and being supported by said outer tube, and the other end of said wire shaped member extending to the proximal end portion of said outer tube.

6. The apparatus according to claim 5, wherein said angle adjusting means includes a wire having one end fixed to a tip end of said distal end portion of said outer tube and another end to which an operation portion is fixed.

7. The apparatus according to claim 5, wherein said angle adjusting means further includes:
    a second tubular passage formed in said outer tube; and
    a second wire having a bent end portion removably inserted in the second tubular passage.

8. The apparatus according to claim 1, further comprising means for adjusting a length of a part of said inner tube which projects from said opening at the distal end of said outer tube, and for adjusting the relative position of said outer tube and said inner tube.

9. The apparatus according to claim 8, wherein said adjusting means comprises screw means formed on a proximal end portion of said outer tube and on a proximal portion of said inner tube.

10. The apparatus according to claim 1, wherein said cutting means comprises a cutting edge directed toward the proximal end of said outer tube.

11. The apparatus according to claim 1, wherein said blocking member comprises a flexible member.

12. An apparatus for blocking a vein branch, comprising:
    an outer tube including a rigid portion having a bent distal end section, a flexible tubular portion connected to a proximal end of the rigid portion and a tubular passage opened at a distal end of the rigid portion and at a proximal end of the flexible tubular portion;
    cutting means formed on a rear side of the bent distal end section of the rigid portion, for cutting a venous valve of a vein; and
    blocking means slidably inserted in the tubular passage of the outer tube so as to be projected and retracted from an opening formed in the bent distal end section, for blocking a vein branch.

13. The apparatus according to claim 12, wherein said blocking means comprises a balloon catheter slidably inserted into said tubular passage of the outer tube so as to be projected and retracted from said opening at the distal end of said outer tube.

14. The apparatus according to claim 12, wherein said blocking means includes means for injecting a filler in said vein branch.

15. The apparatus according to claim 12, wherein said bent distal end section of said rigid portion has an outlet means formed in a front wall thereof, for injecting fluid forwardly.

16. An apparatus for blocking a vein branch, comprising:
    an outer tube having a tubular passage therethrough, said tubular passage having an opening at a distal end of said outer tube and an opening at a proximal end of said outer tube, and said outer tube having a bent distal end portion which is bent at an angle of from 60° to 120°;
    an inner tube slidably inserted in the tubular passage of said outer tube so as to have a portion which is projected from and retracted from the opening at the distal end of said tubular passage, said inner tube being made of a flexible material, and said inner tube having a storing portion at a distal end thereof;
    a blocking member contained in said storing portion of said inner tube;
    means for pushing out said blocking member from said storing portion into a vessel branch;
    means for measuring a length of the portion of said inner tube which is projected from said opening at the distal end of said outer tube, said measuring means being formed on or as part of said outer tube or said inner tube; and
    said measuring means includes a slit formed in a front wall of the bent distal end portion of said outer tube.

17. The apparatus according to claim 16, wherein said blocking member comprises a flexible member.

* * * * *